(12) United States Patent
Tisdale et al.

(10) Patent No.: US 8,329,646 B2
(45) Date of Patent: Dec. 11, 2012

(54) METHODS FOR THE TREATMENT OF MUSCLE LOSS

(75) Inventors: Michael John Tisdale, Warwickshire (GB); Norman Alan Greenberg, New Hope, MN (US); Helen Laura Eley, Kent (GB); Kevin Burke Miller, Minneapolis, MN (US)

(73) Assignee: Nestec S.A., Vevey (CH)

( * ) Notice: Subject to any disclaimer, the term of this patent is extended or adjusted under 35 U.S.C. 154(b) by 475 days.

(21) Appl. No.: 12/095,477

(22) PCT Filed: Nov. 28, 2006

(86) PCT No.: PCT/US2006/045497
§ 371 (c)(1),
(2), (4) Date: Sep. 15, 2008

(87) PCT Pub. No.: WO2007/064618
PCT Pub. Date: Jun. 7, 2007

(65) Prior Publication Data
US 2009/0105123 A1 Apr. 23, 2009

(51) Int. Cl.
*A61K 38/02* (2006.01)
(52) U.S. Cl. .................. 514/5.5; 514/21.91; 562/575
(58) Field of Classification Search .............. 514/5.5, 514/21.91; 562/575
See application file for complete search history.

(56) References Cited

U.S. PATENT DOCUMENTS

| | | | |
|---|---|---|---|
| 4,491,589 A * | 1/1985 | Dell et al. ............... | 514/400 |
| 4,677,121 A | 6/1987 | Walser et al. | |
| 4,780,475 A | 10/1988 | Cerra et al. | |
| 5,087,472 A * | 2/1992 | Nissen ................. | 426/623 |
| 5,716,926 A | 2/1998 | Beale et al. | |
| 5,817,695 A * | 10/1998 | Pellico ................... | 514/558 |
| 6,051,236 A * | 4/2000 | Portman ................ | 424/725 |
| 6,077,828 A * | 6/2000 | Abbruzzese et al. .... | 514/5.5 |
| 6,184,226 B1 * | 2/2001 | Chakravarty et al. ... | 514/266.22 |
| 6,410,540 B1 * | 6/2002 | Goehring et al. ....... | 514/252.13 |
| 6,503,506 B1 | 1/2003 | Germano | |
| 7,199,124 B2 * | 4/2007 | Ohkawa et al. .......... | 514/256 |
| 7,744,930 B2 * | 6/2010 | Fisher et al. ............ | 424/725 |
| 7,790,688 B2 * | 9/2010 | Wolfe et al. ............. | 514/23 |
| 2003/0119888 A1 | 6/2003 | Allen | |
| 2005/0181069 A1 | 8/2005 | McCleary | |
| 2005/0187267 A1 | 8/2005 | Hamann et al. | |

FOREIGN PATENT DOCUMENTS

| | | |
|---|---|---|
| WO | WO 01/56402 | 8/2001 |
| WO | WO 03/048206 | 6/2003 |
| WO | WO 2006/021409 | 3/2006 |

OTHER PUBLICATIONS

May, Diabetes/Metabolism Reviews 5(3) 227-245, 1989.*
Chua, J. Biol. Chem 254, 8358-62, 1979.*
Jammi, Narasimham et al., "Small molecule inhibitors of the RNA-dependent protein kinase," Department of Chemisty, University of Utah, vol. 308, No. 1, Aug. 15, 2003, pp. 50-57.
Lynch, Jordan , "Novel therapies for sarcopenia: ameliorating age-related changes in skeletal muscle," Department of Physiology, Univeristy of Melbourn, vol. 12, No. 1, 2002.
May, Michael et al., "Effects of Branched-Chain Amino Acids on Protein Turnover," Department of Internal Medicine, Vanderbilt University, vol. 5, No. 3, May 1989, pp. 227-245.
Muscaritoli, M et al., "Prevention and treatment of cancer cachexia: New insights into an old problem," Dept of Clinical Medicine, vol. 42, No. 1, Jan. 2006, pp. 31-41.
Smith et al., "Mech. of the Attenuation of Proteolysis-Inducing Factor Stim Protein Deg in Muscle by B-Hydroxy-B-Methylbutyrate," AACR, v. 64, No. 23, Dec. 1, 2004, pp. 8731-8735.

* cited by examiner

*Primary Examiner* — David Lukton
(74) *Attorney, Agent, or Firm* — K&L Gates LLP

(57) ABSTRACT

The invention provides methods for treating muscle loss in an individual. In one embodiment, the invention includes administering to an individual an effective amount of a branched chain amino acid (BCAA), a BCAA precursor, a BCAA metabolite, a BCAA-rich protein, a protein manipulated to enrich the BCAA content or any combination thereof. The invention further provides nutritional products for such administration, including orally-administrable nutritional products.

39 Claims, 6 Drawing Sheets

Mechanisms of Cancer Cachexia

Mechanisms of Cancer Cachexia

METHODS FOR THE TREATMENT OF MUSCLE LOSS

BACKGROUND OF THE INVENTION

1. Technical Field

The invention relates generally to the treatment of muscle loss in a mammal, and more particularly, to the administration of one or more branched chain amino acid(s) (BCAA), a BCAA precursor, a BCAA metabolite, a BCAA-rich protein, a protein manipulated to enrich the BCAA content or any combination thereof in the treatment of such muscle loss. The invention further relates to nutritional formulations suitable for such administration.

2. Background Art

Amino acids are the monomeric building blocks of proteins, which in turn comprise a wide range of biological compounds, including enzymes, antibodies, hormones, transport molecules for ions and small molecules, collagen, and muscle tissues. Amino acids are considered hydrophobic or hydrophilic, based upon their solubility in water, and, more particularly, on the polarities of their side chains. Amino acids having polar side chains are hydrophilic, while amino acids having non-polar side chains are hydrophobic. The solubilities of amino acids, in part, determines the structures of proteins. Hydrophilic amino acids tend to make up the surfaces of proteins while hydrophobic amino acids tend to make up the water-insoluble interior portions of proteins.

Of the common 20 amino acids, nine are considered indispensable (essential) in humans, as the body cannot synthesize them. Rather, these nine amino acids must be obtained through an individual's diet. A deficiency of one or more amino acids can cause a negative nitrogen balance. A negative nitrogen balance, for example, is wherein more nitrogen is excreted than is administered. Such a condition can lead to disruption of enzymatic activity and the loss of muscle mass.

A number of muscle-wasting conditions have been identified for which treatment with amino acid supplements has proved beneficial. For example, cachexia is a severe body wasting condition characterized by marked weight loss, anorexia, asthenia, and anemia. Cachexia is a common feature of a number of illnesses, such as cancer, sepsis, chronic heart failure, rheumatoid arthritis, and acquired immune deficiency syndrome (AIDS). Other muscle wasting diseases and disorders are known, including, for example, sarcopenia, an age-related loss of muscle mass.

Proteolysis-Inducing Factor (PIF)

It has been found that certain tumors may induce cachexia through the production of a 24 kDa glycoprotein called proteolysis-inducing factor (PIF). One proposed mechanism of action of PIF is to decrease protein synthesis; another proposed mechanism of PIF is an activation of protein degradation; a third proposed mechanism is a combination of the aforementioned decrease in protein synthesis and activation of protein degradation. It has been hypothesized that the decreased protein synthesis associated with PIF is the result of PIF's ability to block the translation process of protein synthesis. Another factor, Angiotensin II (Ang II) has shown similar effects and may be involved in the muscle wasting observed in some cases of cachexia.

The original role of PIF in the ubiquitin-proteosome pathway is known. PIF produces an increased release of arachadonic acid, which is then metabolized to prostaglandins and 15-hydroxyeicosatetraenoic acid (15-HETE). 15-HETE has been shown to produce a significant increase in protein degradation and nuclear binding of the transcription factor NF-κB (a nuclear factor that binds the kappa immunoglobulin light chain gene enhancer in B cells).

Regulation of Protein Synthesis Via Translation Initiation

The role of PIF in the inhibition of protein synthesis is hypothesized to be due to PIF's theorized ability to block translation via RNA-dependent protein kinase (PKR) activation of downstream factors. Inhibition of protein synthesis by PIF is attenuated by insulin at physiological concentrations and below. This suggests that PIF may inhibit protein synthesis at the initiation stage of translation, since insulin regulates protein synthesis through activation of the messenger RNA (mRNA) binding steps in translation initiation.

There are two steps in the initiation of translation that are subject to regulation: (1) the binding of initiator methionyl-transfer RNA (met-tRNA) to the 40s ribosomal subunit; and (2) the binding of mRNA to the 43s preinitiation complex.

In the first step, met-tRNA binds to the 40s ribosomal subunit as a ternary complex with eukaryotic initiation factor 2 (eIF2) and guanosine triphosphate (GTP). Subsequently, the GTP bound to eIF2 is hydrolyzed to guanosine diphosphate (GDP) and eIF2 is released from the ribosomal subunit in a GDP-eIF2 complex. The eIF2 must then exchange the GDP for GTP to participate in another round of initiation. This occurs through the action of another eukaryotic initiation factor, eIF2B, which mediates guanine nucleotide exchange on eIF2. eIF2B is regulated by the phosphorylation of eIF2 on its alpha subunit, which converts it from a substrate into a competitive inhibitor of eIF2B.

In the second step, the binding of mRNA to the 43s preinitiation complex requires a group of proteins collectively referred to as eIF4F, a multisubunit complex consisting of eIF4A (an RNA helicase), eIF4B (which functions in conjunction with eIF4A to unwind secondary structure in the 5' untranslated region of the mRNA), eIF4E (which binds the m7GTP cap present at the 5' end of the mRNA), and eIF4G (which functions as a scaffold for eIF4E, eIF4A, and the mRNA). Collectively, the eIF4F complex serves to recognize, unfold, and guide the mRNA to the 43s preinitiation complex. The availability of the eIF4E for the eIF4F complex formation appears to be regulated by the translational repressor eIF4E-binding protein 1 (4E-BP1). 4E-BP1 competes with eIF4G to bind eIF4E and is able to sequester eIF4E into an inactive complex. The binding of 4E-BP1 is regulated through phosphorylation by the kinase mammalian target of rapamycin (mTOR), where increased phosphorylation causes a decrease in the affinity of 4E-BP1 for eIF4E.

It is believed that mTOR is activated by phosphorylation and inhibition of the tuberous sclerosis complex (TSC) 1-TSC2 complex via signaling through the phosphatidylinositol 3 kinase (PI3K)/serine/threonine kinase pathway (PI3K/AKT pathway). mTOR also phosphorylates p70S6 kinase, which phosphorylates ribosomal protein S6, which is believed to enhance the translation of mRNA with an uninterrupted string of pyrimidine residues adjacent to the 5' cap structure. Proteins encoded by such mRNA include ribosomal proteins, translation elongation factors, and poly-A binding proteins.

Anabolic Factors Involved in Translation Initiation

Many studies have shown that anabolic factors, such as insulin, insulin-like growth factors (IGFs), and amino acids increase protein synthesis and cause muscle hypertrophy. Branched chain amino acids (BCAAs), particularly leucine, can initiate signal transduction pathways that modulate translation initiation. Such pathways often include mTOR. Other studies have demonstrated that mitogenic stimuli, such as insulin and BCAAs, signal via eIF2. As such, amino acid starvation results in an increased phosphorylation of eIF2-α and a decrease in protein synthesis.

Signaling Pathways Involved in Protein Synthesis and Degradation

As noted above, PIF is known to induce protein degradation via the NF-κB pathway. Therefore, it is plausible that inhibition of protein synthesis by PIF occurs via a common signaling initiation point, which then diverges into two separate pathways, one promoting protein degradation via NF-κB and the other inhibiting protein synthesis through mTOR and/or eIF2.

AKT is a serine/threonine kinase, also known as protein kinase B (PKB). Activation of AKT occurs through direct binding of the inositol lipid products of the PI3K to its pleckstrin homology domain. PI3K-dependent activation of AKT also occurs through phosphoinositide-dependent kinase (PDK1)-mediated phosphorylation of threonine 308, which leads to autophosphorylation of serine 473. Although initially believed to operate as components of distinct signaling pathways, several studies have demonstrated that the NF-κB and AKT signaling pathways converge. Studies have shown that AKT signaling inhibits apoptosis in a variety of cell types in vitro, mediated by its ability to phosphorylate apoptosis-regulating components, including IκK, the kinase involved in NF-κB activation. Thus, activation of AKT stimulates activation of NF-κB. Although this would place AKT upstream of NF-κB activation in the sequence of signaling events, one study reports that AKT may be a downstream target of NF-κB. Overall, this suggests that AKT is involved in a catabolic pathway. Other data, however, suggest that AKT is also involved in anabolic processes through activation of mTOR and the consequent phosphorylation of p70S6 kinase and 4E-BP1, leading to an increase in protein synthesis.

PKR is an interferon-induced, RNA-dependent serine/threonine protein kinase responsible for control of an antiviral defense pathway. PKR may be induced by forms of cellular stress other than interferon. Some evidence suggests that tumor necrosis factor (TNF)-alpha also acts through PKR. Interestingly, both interferon and TNF-alpha have been implicated as causative factors of cachectic states. Following interaction with activating stimuli (e.g., insulin, IGF, BCAAs), PKR has been reported to form homodimers and autophosphorylate. As a result, PKR is able to catalyze the phosphorylation of target substrates, the most well-characterised being the phosphorylation of Serine 51 on the eIF2-α subunit. The eIF2 then sequesters eIF2B, a rate-limiting component of translation, resulting in the inhibition of protein synthesis. Recent studies suggest that PKR physically associates with the IκK complex and stimulates NF-κB-inducing kinase (NIK) while phosphorylating IκK, resulting in its subsequent degradation. Some studies suggest that NF-κB is activated by PKR by a mechanism independent from its eIF2 kinase activity, while other studies indicate that the phosphorylation of eIF2-α is required for the activation of NF-κB.

PKR-like ER-resident kinase (PERK) is another kinase that phosphorylates eIF2-α and activates NF-κB. However, it is unlikely that PIF acts through this pathway, since PERK causes the release of IκK from NF-κB, but not its degradation. In addition, PIF has been shown to cause the degradation of IκK during the activation of NF-κB.

Known Treatments for Muscle Loss

Treatment of conditions such as cachexia often includes nutritional supplementation, and, in particular, amino acid supplementation, in an attempt to increase protein synthesis. The three BCAAs are valine, leucine, and isoleucine. Previously, leucine has been shown to function, not only as a protein building block, but also as an inducer of signal transduction pathways that modulate translation initiation. Our recent novel research suggests that all three of the BCAAs possess the ability to reduce protein degradation and enhance protein translation comparably.

Cachexia is just one of the conditions, disorders, and diseases for which amino acid supplementation has proved beneficial. Amino acid supplementation has also been used to treat diabetes, hypertension, high levels of serum cholesterol and triglycerides, Parkinson's disease, insomnia, drug and alcohol addiction, pain, insomnia, and hypoglycemia. Supplementation with BCAAs, in particular, has been used to treat liver disorders, including compromised liver function, including cirrhosis, gall bladder disorders, chorea and dyskinesia, and kidney disorders, including uremia. BCAA supplementation has also proved successful in the treatment of patients undergoing hemodialysis, resulting in improvements in overall health and mood.

To date, the treatment of muscle loss, including treatments involving nutritional supplementation with amino acids, has focused on the promotion of muscle anabolism. For example, U.S. Patent Application Publication No. 2004/0122097 to Verlaan et al. describes nutritional supplements containing both leucine and protein for promoting the generation of muscle tissue. Leucine precursors, such as pyruvate, and metabolites, such as β-hydroxy-β-methylbutyrate and α-ketoisocaproate, exhibit properties similar to those of leucine. Of note, β-hydroxy-β-methylbutyrate is not produced by humans in any clinically relevant quantities and therefore must be supplemented.

Others have shown that insulin, an anabolic hormone, is capable of promoting protein synthesis when administered in large doses. Thus, known treatment approaches, while providing some benefit to individuals suffering from muscle loss through increased generation of muscle tissue, do not affect muscle loss itself. That is, known methods of treating muscle loss are directed toward increasing muscle anabolism rather than decreasing muscle catabolism.

The amino acids that comprise skeletal muscle are in a constant state of flux where new amino acids, either coming from administration by enteral or parenteral routes or recirculated, are deposited as protein and current proteins are degraded. Loss of muscle mass can be the result of many factors including decreased rate of protein synthesis with normal degradation, increased degradation with normal synthesis or an exacerbation of both reduced synthesis and increased degradation. As a result, therapies aimed at increasing synthesis only address one-half of the problem in muscle wasting disease(s).

Accordingly, there is a need in the art for a method of treating muscle loss that decreases muscle catabolism and, optionally, increases muscle anabolism.

SUMMARY OF THE INVENTION

The invention provides methods for treating muscle loss in an individual. In one embodiment, the invention includes administering to an individual an effective amount of a branched chain amino acid (BCAA), a BCAA precursor, a BCAA metabolite, BCAA-rich protein, protein manipulated to enrich the BCAA content, or any combination thereof. The invention further provides nutritional products for such administration, including orally-administrable nutritional products.

In a first aspect, the invention provides a method of treating muscle loss in an individual, the method comprising: administering to the individual an effective amount of at least one of: a branched chain amino acid (BCAA); a BCAA precursor;

and a BCAA metabolite, a BCAA-rich protein, a protein manipulated to enrich the BCAA content, wherein at least one of the BCAA, BCAA precursor, BCAA metabolite, BCAA-rich protein, and protein manipulated to enrich the BCAA content antagonizes protein catabolism.

In a second aspect, the invention provides an orally-administrable nutritional product comprising at least one of the following: a branched chain amino acid (BCAA); a BCAA precursor, a BCAA metabolite, a BCAA-rich protein, a protein manipulated to enrich the BCAA content, wherein at least one of the BCAA, BCAA precursor, BCAA metabolite, BCAA-rich protein, and protein manipulated to enrich the BCAA content antagonizes protein catabolism.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention.

DETAILED DESCRIPTION

As indicated above, the invention provides methods and related products for the treatment of muscle loss in an individual. More specifically, the methods and products of the invention reduce muscle catabolism, particularly proteolysis-inducing factor (PIF)-mediated muscle catabolism.

As used herein, the terms "treatment" and "treat" refer to both prophylactic or preventive treatment and curative or disease-modifying treatment, including treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as nitrogen imbalance or muscle loss. Consequently, an "effective amount" is an amount that treats a disease or medical condition in an individual or, more generally, provides a nutritional, physiological, or medical benefit to the individual. A treatment can be patient- or doctor-related. In addition, while the terms "individual" and "patient" are often used herein to refer to a human, the invention is not so limited. Accordingly, the terms "individual" and "patient" refer to any mammal suffering from or at risk for a medical condition, such as muscle loss.

Experimental Data

In order to determine the efficacy of branched chain amino acids (BCAAs) and other agents in reducing muscle catabolism, murine $C_2C_{12}$ myotubes were exposed to PIF or Angiotensin II in combination with amino acids (including BCAAs), insulin, insulin-like growth factor-1 (IGF-1), and a PKR inhibitor. PIF was extracted and purified from MAC16 tumors as described by Smith et al., *Effect of a Cancer Cachectic Factor on Protein Synthesis/Degradation in Murine C2C12 Myoblasts: Modulation by Eicosapentaenoic Acid*, Cancer Research, 59:5507-13 (1999), which is hereby incorporated by reference. Protein degradation was determined using the method described by Whitehouse et al., *Increased Expression of the Ubiquitin-Proteasome Pathway in Murine Myotubes by Proteolysis-Inducing Factor (PIF) is Associated with Activation of the Transcription Factor NF-κB*, British Journal of Cancer, 89:1116-22 (2003), which is also hereby incorporated by reference.

Figure 1:
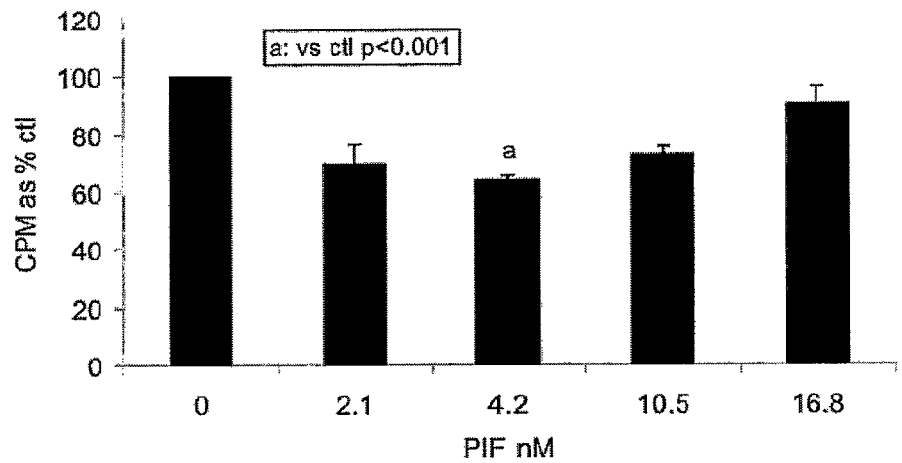
FIG. 1 shows a graph of the depression of protein synthesis by proteolysis inducing factor (PIF) at various concentrations.

FIG. 1 shows a graph of the depression of protein synthesis of PIF at increasing concentrations, measured in counts per minute (CPM) as a percentage of a control containing no PIF. A significant reduction in protein synthesis is noted, with a maximum depression of protein synthesis occurring at a PIF concentration of 4.2 nM. The measured proteolytic activity of PIF can be more specifically described as ubiquitin-like degradation activity.

Figure 2:
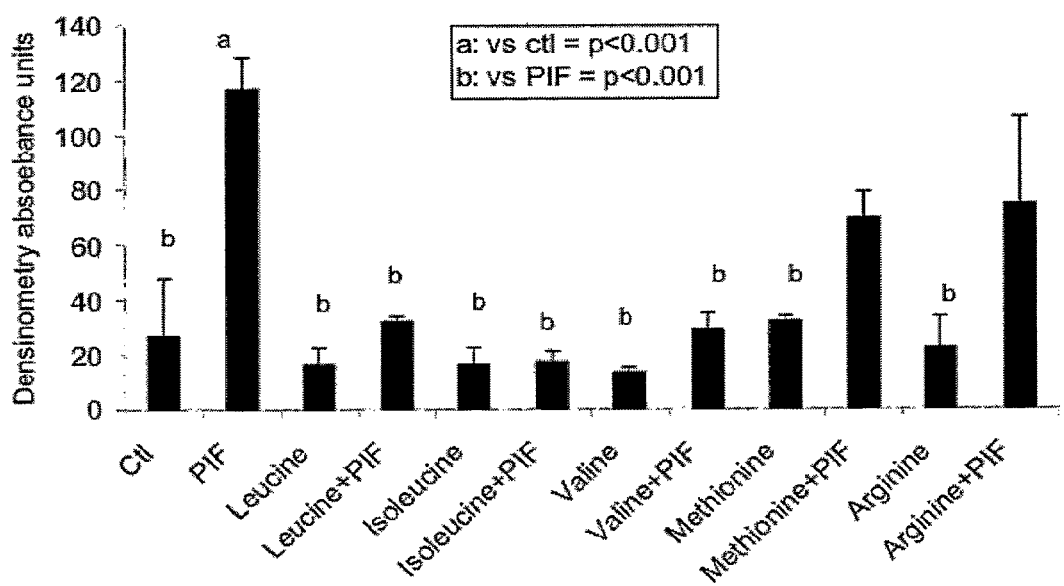
FIG. 2 shows a graph of the effect of amino acids on the phosphorylation of eIF2-α and PIF.

FIG. 2 shows a graph of the densitometric analysis of Western blots of phosphorylated eIF2-α in $C_2C_{12}$ myotubes incubated with PIF, leucine, isoleucine, valine, methionine, and arginine, both alone and in combination with PIF. The control sample was incubated only in phosphate buffered saline (PBS). As can be seen in FIG. 2, PIF increases phosphorylation of eIF2-α significantly, compared to the control. Each of the amino acids reduced eIF2-α phosphorylation in the presence of PIF, compared to PIF alone. However, the BCAAs (i.e., leucine, isoleucine, and valine) reduced such phosphorylation to about the level of the control or below, while methionine- and arginine-induced phosphorylation levels were greater than that of the control. Surprisingly, unlike known treatment methods directed toward increasing protein synthesis, and where leucine exhibits greater efficacy than the other BCAAs, these data show that all BCAAs are about equally effective in reducing PIF-induced phosphorylation of eIF2-α. In fact, the phosphorylation levels resulting from isoleucine and valine incubation were not different from that observed with leucine incubation.

Figure 3:
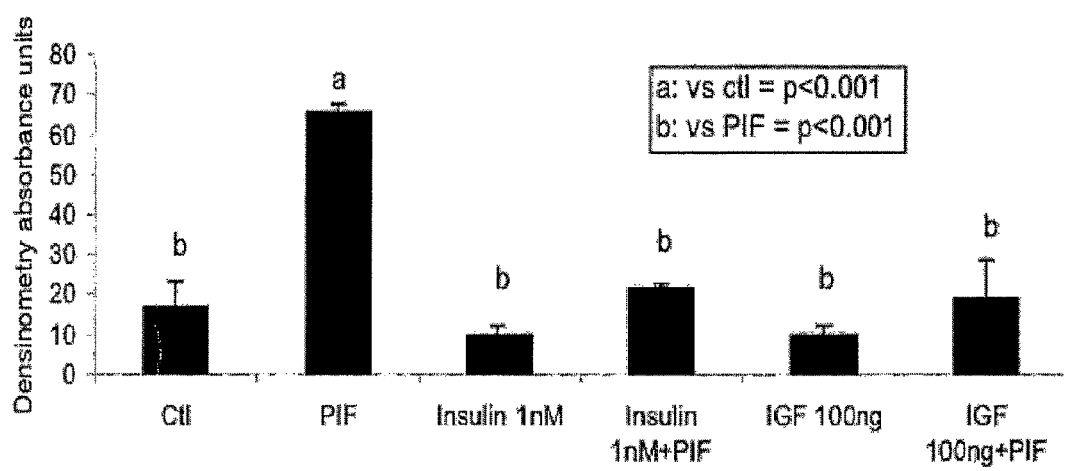
FIG. 3 shows a graph of the effect of insulin and insulin-like growth factor 1 (IGF) on the phosphorylation of eIF2-α of PIF.

FIG. 3 shows the results of similar experiments involving the incubation of insulin and IGF-1, alone and in combination with PIF. Both insulin and IGF-1 significantly reduced eIF2-α phosphorylation in the presence of PIF, compared to PIF alone. Thus, the ability of BCAAs to decrease PIF-mediated protein degradation may be supplemented or enhanced by the addition of insulin and/or IGF-1 or by treatments that increase the level of insulin and/or IGF-1.

Figure 4:
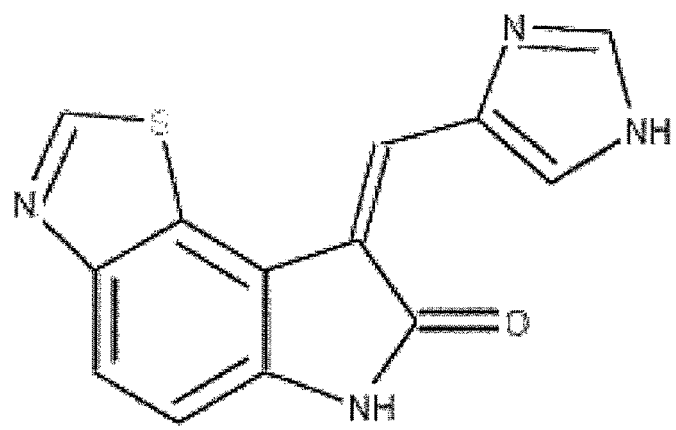
FIG. 4 shows the structure of an RNA-dependent protein kinase (PKR) inhibitor suitable for use in the present invention.
Figure 5:
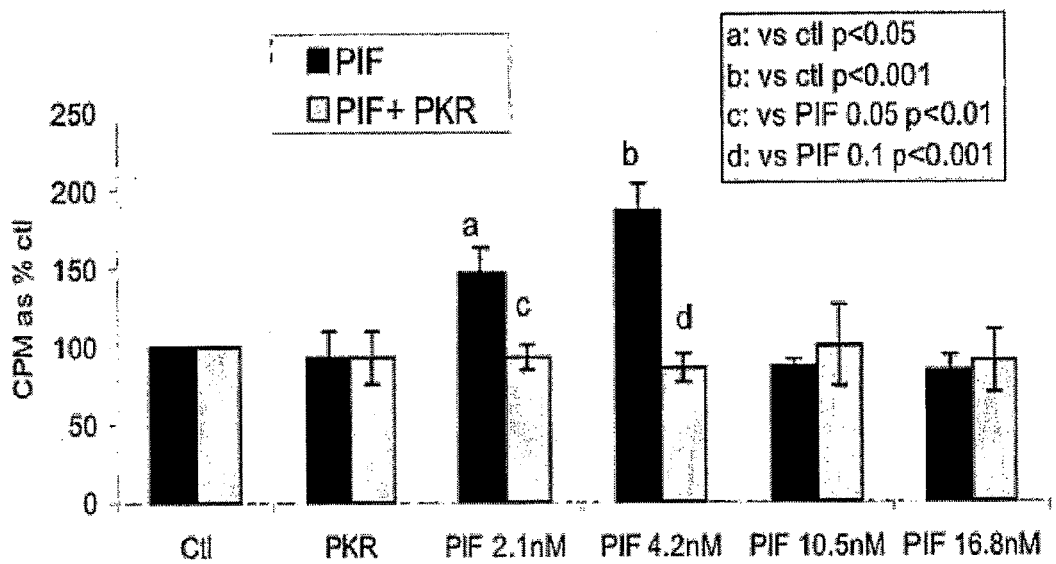
FIG. 5 shows a graph of the effect of the PKR inhibitor of FIG. 4 on the proteolytic activity of PIF.
Figure 6:
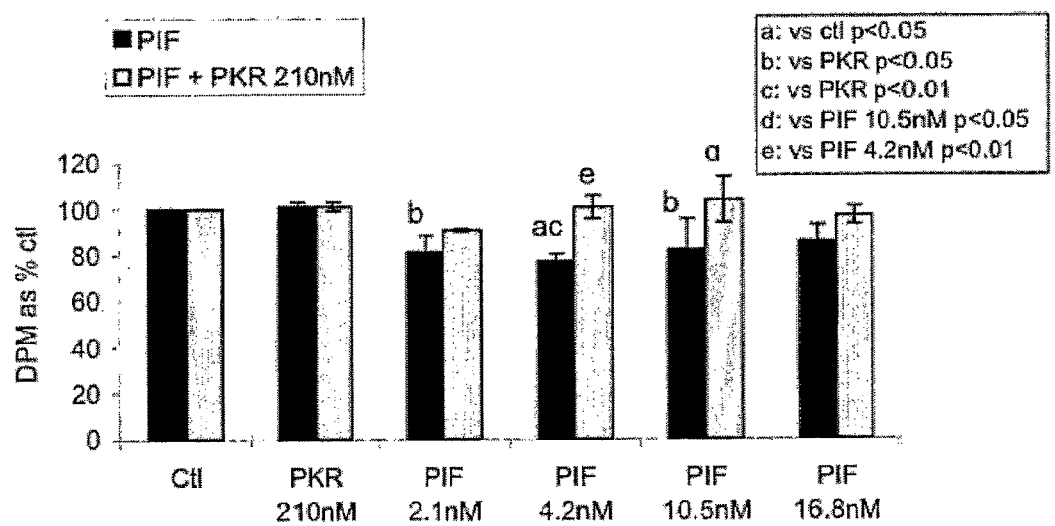
FIG. 6 shows a graph of the effect of the PKR inhibitor of FIG. 4 in reversing a PIF-mediated reduction in protein synthesis.

FIG. 4 shows the structure of a PKR inhibitor useful in both decreasing PIF-induced protein degradation and increasing protein synthesis which was used as a positive control of PKR inhibition. FIGS. 5-8 show the results of experiments involving the incubation of the PKR inhibitor in combination with either PIF or Angiotensin II. In FIG. 5, it can be seen that while PIF increased protein degradation up to 87% when incubated alone, the addition of the PKR inhibitor reversed protein degradation levels back to about those of the control. Similarly, in FIG. 6, it can be seen that while PIF reduced protein synthesis up to about 25% when incubated alone, the addition of the PKR inhibitor reversed protein synthesis levels back to about those of the control.

Figure 7:
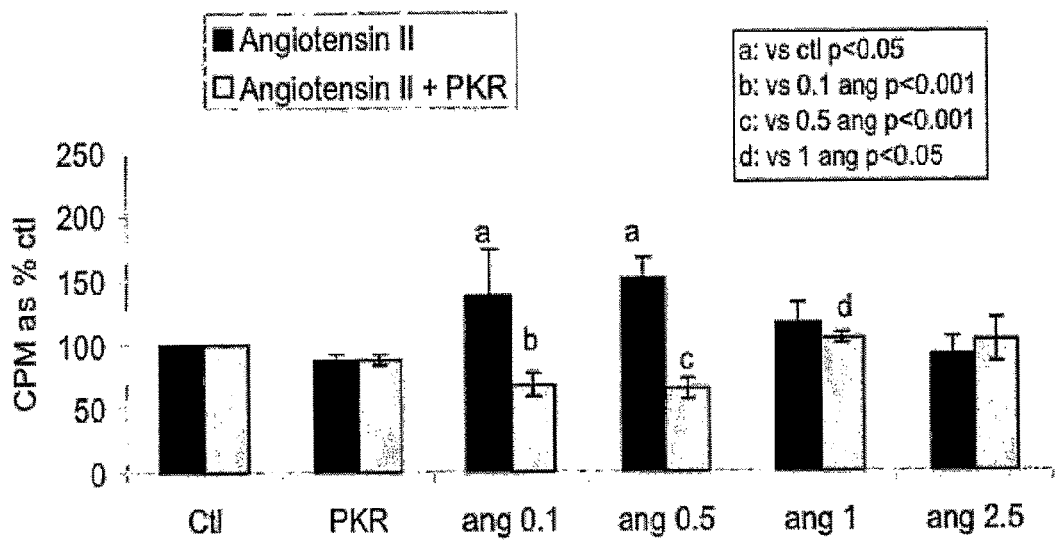
FIG. 7 shows a graph of the effect of the PKR inhibitor of FIG. 4 on the proteolytic activity of Angiotensin II.
Figure 8:
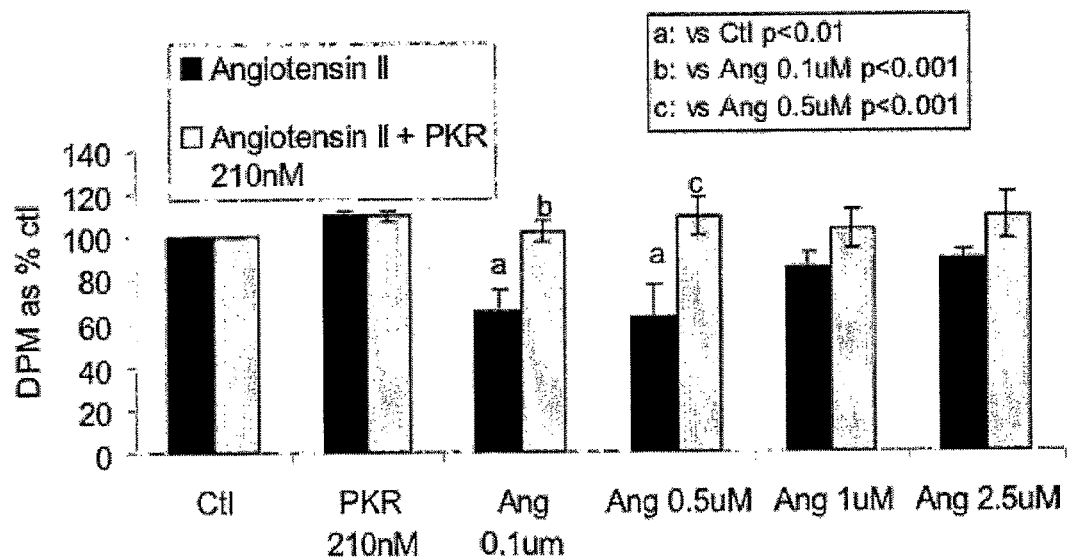
FIG. 8 shows a graph of the effect of the PKR inhibitor of FIG. 4 in reversing an Angiotensin II-mediated reduction in protein synthesis.

FIGS. 7 and 8 show similar results upon the incubation of the PKR inhibitor with Angiotensin II. In FIG. 7, Angiotensin increased protein degradation up to about 51%, compared to the control. The addition of the PKR inhibitor reversed this trend, maintaining protein degradation levels at about that of the control. Similarly, in FIG. 8, Angiotensin II reduced protein synthesis by about 40% compared to the control, while the addition of the PKR inhibitor maintained protein synthesis levels at about that of the control.

The PKR inhibitor attenuated the actions of PIF and Angiotensin II in both protein degradation and protein synthesis. This suggests that both PIF and Angiotensin II mediate their effects through similar mechanisms and through a common mediator, likely involving PKR. More specifically, these results suggest that PIF activates PKR, which in turn causes phosphorylation of eIF2-α, inhibiting the binding of initiator methionyl-tRNA (met-tRNA) to the 40s ribosomal subunit. BCAAs, insulin, and IGF-1 attenuated the phosphorylation of eIF2-α caused by PIF, further supporting the hypothesis that PIF upregulates phosphorylation of eIF2-α to inhibit protein synthesis. Since PKR can inhibit protein synthesis and activate NF-κB, which leads to protein degradation, PKR is likely an early component in the signaling pathway of PIF.

There is also evidence that PKR is involved in the regulation of 4E-BP1 phosphorylation. Thus, if PIF does signal through PKR, it is likely that it can also reduce protein synthesis through PKR-mediated activation of the serine/threonine phosphatase PP2A, which can bring about the dephosphorylation of 4E-BP1, which in turn sequesters eIF4E into an inactive complex, preventing the formation of the 43s pre-initiation complex.

Figure 9:
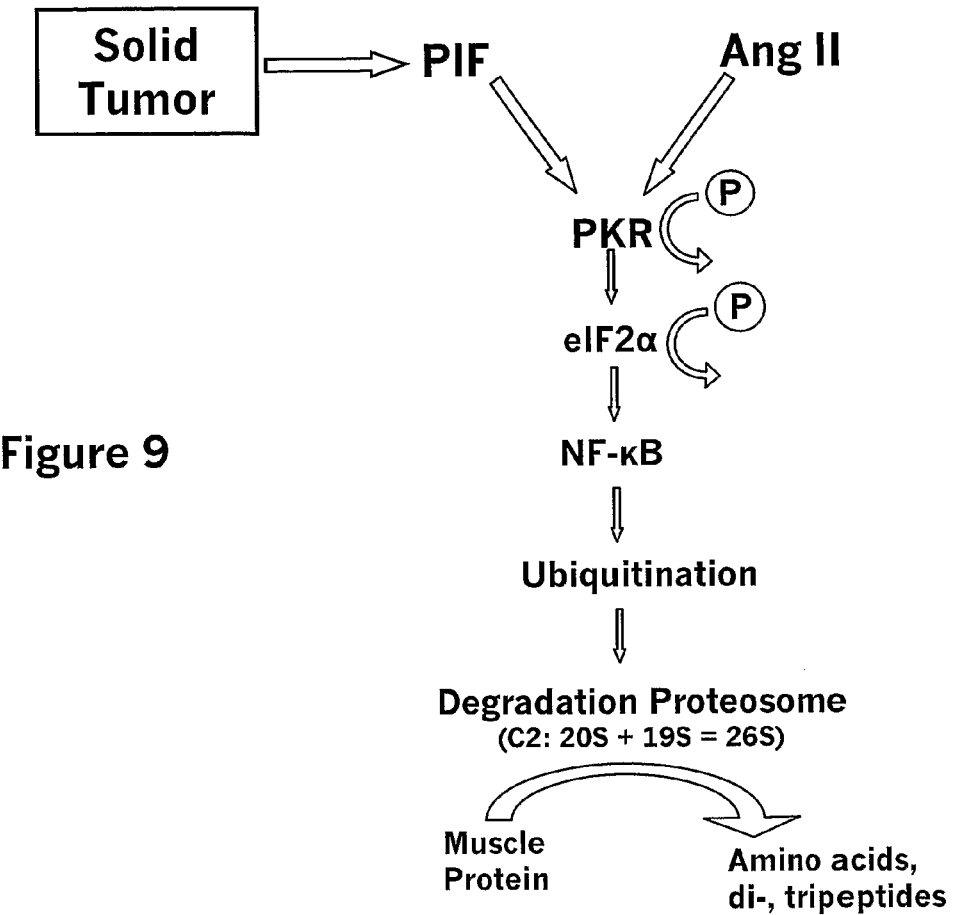
FIG. 9 shows an alternative mechanism of protein degradation caused by proteolysis inducing factor (PIF) and inhibited by branch chain amino acids, insulin and IGF-1.

FIG. 9 shows an alternative mechanism. Both proteolysis inducing factor (PIF) and angiotensin II (Ang II) decrease protein synthesis by 40%, and the concentrations of both agents that are maximally effective in the depression of protein synthesis are the same as those that are maximally effective in the induction of protein degradation. The results suggest that both insulin and IGF1, at least partly, attenuate the protein degradation induced by PIF through inhibition of PKR and/or eIF2α phosphorylation. The mechanism of activation by PIF and Ang II may be through PACT (protein activator of interferon-induced protein kinase), a cellular protein activator of PKR, although PIF is also a polyanionic molecule, and thus may activate directly. Regardless, phosphorylation of eIF2α by PIF and Ang II seems to occur through PKR, since a PKR inhibitor attenuated the inhibitory effect of both agents on protein synthesis. The effect of both PIF and Ang II on protein translation appears to arise from an increased phosphorylation of eIF2α.

The inhibition of protein synthesis in apoptosis by tumor necrosis factor-α (TNF-α) is also associated with increased phosphorylation of eIF2α. Further support for the role of eIF2α phosphorylation in the inhibition of protein synthesis by PIF and Ang II is provided by the observation that both insulin and IGF1, which were effective in suppressing the inhibition of protein synthesis, completely attenuated the induction of eIF2α phosphorylation. Data collected suggests that the BCAAs also work through the same mechanism to inhibit the degradation pathway initiated by PIF. This study provides the first evidence of a relationship between the depression of protein synthesis in skeletal muscle by PIF (and Ang II), through activation of PKR, and eIF2α phosphorylation, and the enhanced degradation of the myofibrillar protein myosin, through activation of NF-κB resulting in an increased expression and activity of the ubiquitin-proteasome proteolytic pathway. This suggests that agents which target PKR (e.g., BCAAs) may be effective in the treatment of muscle atrophy in cancer cachexia.

Figure 10:
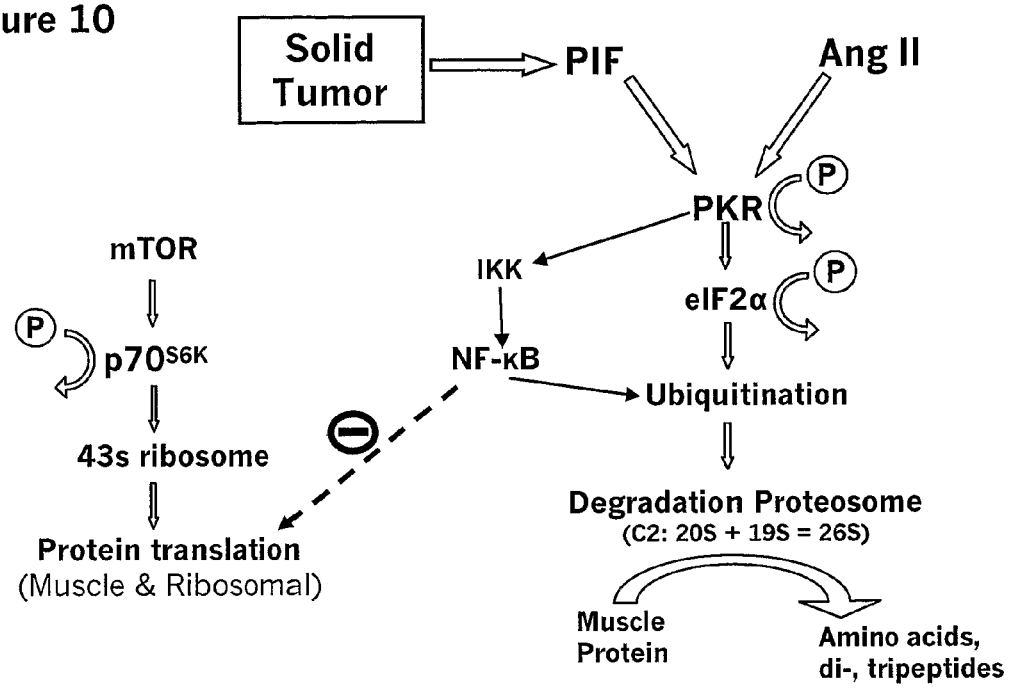
FIG. 10 shows a further alternative mechanism of protein degradation caused by proteolysis inducing factor (PIF) through activation of PKR and eIF2α that is inhibited by branch chain amino acids, insulin and IGF-1.

FIG. 10 shows a further alternative mechanism. As previously stated, both proteolysis inducing factor (PIF) and angiotensin II (Ang II) increase protein degradation through phosphorylation of PKR and/or eIF2α. NF-κB may be activated by PIF or a downstream mediator of PIF (PKR and/or eIF2α) which occurs through the release of NF-κB. In this further alternative mechanism, NF-κB is not part of the same phosphorylation cascade despite having the same target to promote ubiquitin-tagging of proteins to be degraded.

Together, the data above support a number of novel aspects of the present invention. First, BCAAs may be employed to treat muscle loss in an individual by antagonizing protein catabolism mediated by PIF and/or Angiotensin II through inhibiting the activation of PKR and/or eIF2α. Second, each of the BCAAs is equally effective in such antagonization. Third, the co-administration of insulin, IGF-1, and/or a PKR inhibitor, or the use of treatments to increase level of either or both of insulin and IGF-1, may increase the efficacy of BCAA treatments by further antagonizing protein catabolism, enhancing protein synthesis, or both.

Nutritional products according to the invention may, therefore, include BCAAs, alone or in combination with insulin, IGF-1, and/or a PKR inhibitor. BCAAs may be administered in their free forms, as dipeptides, as tripeptides, as polypeptides, as BCAA-rich protein, and/or as protein manipulated to enrich the BCAA content. Dipeptides, tripeptides and polypeptides may include two or more BCAAs. Where non-BCAAs are included in a dipeptide, tripeptide, or polypeptide preferred amino acids include alanine and glycine, but non-BCAAs may be any of the dispensable or indispensable (essential or non-essential) amino acids. For example, preferred dipeptides include, but are not limited to, alanyl-leucine, alanyl-isoleucine, alanyl-valine, glycyl-leucine, glycyl-isoleucine, and glycyl-valine.

Nutritional products according to the invention may similarly include precursors and/or metabolites of BCAAs, particularly precursors and/or metabolites of leucine, in addition to or in place of BCAAs. Such products may further include any number of additional ingredients, including, for example, a protein, a fiber, a fatty acid, a vitamin, a mineral, a sugar, a carbohydrate, a flavor agent, a medicament, and a therapeutic agent.

The nutritional products of the present invention may be administered orally, via a feeding tube, or parenterally. Such products may be used in the treatment of an individual suffering from any number of muscle wasting diseases, disorders, or conditions, or any disease, disorder, or condition with which muscle loss is associated, including, for example, cachexia, cancer, tumor-induced weight loss, sepsis, chronic heart failure, rheumatoid arthritis, acquired immune deficiency syndrome (AIDS), sarcopenia, diabetes, hypertension, high levels of serum cholesterol, high levels of triglycerides, Parkinson's disease, insomnia, drug addiction, alcohol addiction, pain, insomnia, hypoglycemia, compromised liver function, including cirrhosis, gall bladder disorders, chorea, dyskinesia, and a kidney disorder, including uremia.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of treating muscle loss in an individual, the method comprising:
   administering to the individual a nutritional product comprising an effective amount of:
   (i) at least one of a branched chain amino acid (BCAA), a BCAA precursor, a BCAA metabolite, a BCAA-rich protein; or
   a protein manipulated to enrich the BCAA content, wherein at least one of the BCAA, BCAA precursor, BCAA metabolite, BCAA rich protein, and a protein manipulated to enrich the BCAA content, antagonizes protein catabolism; and
   (ii) an RNA-dependent protein kinase (PKR) inhibitor, wherein the PKR is an interferon-induced serine/threonine protein kinase.

2. The method of claim 1, wherein administering step includes administering a plurality of BCAAs.

3. The method of claim 1, wherein the BCAA is selected from a group consisting of: leucine, isoleucine, and valine.

4. The method of claim 1, wherein at least one of the BCAA, the BCAA precursor, BCAA metabolite, a BCAA-rich protein; or the protein manipulated to enrich the BCAA content promotes protein synthesis.

5. The method of claim 1, wherein the BCAA is administered as at least one of: a dipeptide, tripeptide, polypeptide or a peptide enriched in BCAAs.

6. The method of claim 5, wherein the dipeptide includes two branched chain amino acids.

7. The method of claim 5, wherein said dipeptide, tripeptide or polypeptide comprises at least one dispensable or indispensable amino acid, wherein at least one indispensable amino acid is a BCAA.

8. The method of claim 5, wherein the dipeptide includes one of alanine and glycine.

9. The method of claim 5, wherein the dipeptide is selected from a group consisting of: alanyl-leucine, alanyl-isoleucine, alanyl-valine, glycyl-leucine, glycyl-isoleucine, and glycyl-valine.

10. The method of claim 5, wherein the tripeptide includes at least two BCAAs.

11. The method of claim 1, wherein the BCAA precursor includes pyruvate.

12. The method of claim 1, wherein the BCAA metabolite is selected from a group consisting of: β-hydroxy-β-methyl-butyrate and β-ketoisocaproate.

13. The method of claim 1, further comprising:
   administering to the individual at least one of: insulin and insulin-like growth factor 1 (IGF-1).

14. The method of claim 1, wherein the PKR inhibitor has the structure:

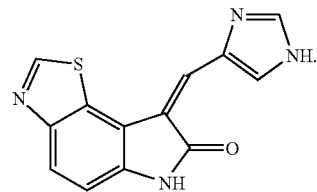

15. The method of claim 1, further comprising:
   treating the individual to raise a level of at least one of the following: insulin and IGF-1.

16. The method of claim 1, wherein at least one of the following is administered in an orally-administrable nutritional product: the BCAA, the BCAA precursor, the BCAA metabolite, the BCAA-rich protein; or the protein manipulated to enrich the BCAA content.

17. The method of claim 16, wherein the orally-administrable nutritional product further includes at least one of the following: a protein, a fiber, a fatty acid, a vitamin, a mineral, a sugar, a carbohydrate, a flavor agent, a medicament, and a therapeutic agent.

18. The method of claim 1, wherein at least one of the following is administered via a feeding tube: the BCAA, the BCAA precursor, the BCAA metabolite, the BCAA-rich protein; or the protein manipulated to enrich the BCAA content.

19. The method of claim 1, wherein at least one of the following is administered parenterally: the BCAA, the BCAA precursor, the BCAA metabolite, and dipeptide or tripeptide containing at least one BCAA.

20. The method of claim 1, wherein the protein catabolism is mediated directly or indirectly by:
   (a) proteolysis inducing factor (PIF);
   (b) Angiotensin II; (C) PKR;
   (d) eIF2α; or
   (e) a combination thereof.

21. The method of claim 1, wherein the individual has at least one of the following: cachexia, cancer, tumor-induced weight loss, sepsis, chronic heart failure, rheumatoid arthritis, acquired immune deficiency syndrome (AIDS), sarcopenia, diabetes, hypertension, high levels of serum cholesterol, high levels of triglycerides, Parkinson's disease, insomnia, drug addiction, alcohol addiction, pain, insomnia, hypoglycemia, compromised liver function, including cirrhosis, gall bladder disorders, chorea, dyskinesia, and a kidney disorder, including uremia.

22. A nutritional product comprising:
   (i) at least one of a branched chain amino acid (BCAA), a BCAA precursor, a BCAA metabolite, a BCAA-rich protein; or
   a protein manipulated to enrich the BCAA content, wherein at least one of the BCAA, BCAA precursor, BCAA metabolite, BCAA-rich protein, and a protein manipulated to enrich the BCAA content antagonizes protein catabolism; and
   (ii) an RNA-dependent protein kinase (PKR) inhibitor, wherein the PKR is an interferon-induced serine/threonine protein kinase.

23. The product of claim 22, comprising a plurality of BCAAs.

24. The product of claim 22, wherein the BCAA is selected from a group consisting of: leucine, isoleucine, and valine.

25. The product of claim 22, wherein at least one of the BCAA, the BCAA precursor, the BCAA metabolite, the BCAA-rich protein, or the protein manipulated to enrich the BCAA content further promotes protein synthesis.

26. The product of claim 22, wherein the BCAA is administered as least one of a dipeptide, tripeptide or polypeptide.

27. The product of claim 26, wherein the dipeptide includes two branched chain amino acids.

28. The product of claim 26, wherein said dipeptide, tripeptide or polypeptide comprises at least one dispensable or indispensable amino acid, wherein at least one indispensable amino acid is a BCAA.

29. The product of claim 26, wherein the dipeptide includes one of alanine and glycine.

30. The product of claim 26, wherein the dipeptide is selected from a group consisting of: alanyl-leucine, alanyl-isoleucine, alanyl-valine, glycyl-leucine, glycyl-isoleucine, and glycyl-valine.

31. The product of claim 26, wherein the tripeptide includes at least two BCAAs.

32. The product of claim 22, wherein the BCAA precursor includes pyruvate.

33. The product of claim 22, wherein the BCAA metabolite is selected from a group consisting of: β-hydroxy-β-methyl-butyrate and β-ketoisocaproate.

34. The product of claim 22, further comprising at least one of: insulin and insulin-like growth factor 1 (IGF-1).

35. The product of claim 22, wherein the PKR inhibitor has the structure:

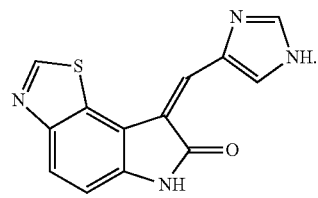

36. The product of claim 22, further comprising at least one of the following: a protein, a fiber, a fatty acid, a vitamin, a mineral, a sugar, a carbohydrate, a flavor agent, a medicament, and a therapeutic agent.

37. The product of claim 22, wherein the protein catabolism is mediated directly or indirectly by:
 (a) proteolysis inducing factor (PIF);
 (b) Angiotensin II;
 (c) PKR;
 (d) eIF2α; or
 (e) a combination thereof.

38. The product of claim 22, wherein the product may be administered orally or via a feeding tube.

39. The product of claim 22, wherein at least one of the following is administered parenterally: the BCAA, the BCAA precursor, the BCAA metabolite, and dipeptide or tripeptide containing at least one BCAA.

* * * * *